United States Patent [19]

Takahashi et al.

[11] Patent Number: 5,008,266
[45] Date of Patent: Apr. 16, 1991

[54] 4(3H)-UINAZOLINONE DERIVATIVES AND PHARMACEUTICAL COMPOSITIONS

[75] Inventors: Toshihiro Takahashi, Kawagoe; Tatsuo Horaguchi, Fujimi; Koichi Nakamaru, Ohimachi; Yoshikuni Suzuki, Ohmiya, all of Japan

[73] Assignee: Nisshin Flour Milling Co., Ltd., Tokyo, Japan

[21] Appl. No.: 373,024

[22] Filed: Jul. 26, 1989

Related U.S. Application Data

[62] Division of Ser. No. 373,024, Jan. 26, 1988, Pat. No. 4,861,780.

[30] Foreign Application Priority Data

Jan. 30, 1987 [JP] Japan .................................. 62-20123
Aug. 20, 1987 [JP] Japan .................................. 62-205071

[51] Int. Cl.$^5$ .................. A61K 31/505; C07D 401/12
[52] U.S. Cl. .................................... 514/259; 544/116; 544/284; 544/285
[58] Field of Search ...................... 544/284, 285, , 116; 514/259, 234.5

[56] References Cited

U.S. PATENT DOCUMENTS 4,833,144  5/1989  Takahashi et al. ................... 544/284
4,861,780  8/1989  Toshihiro et al. .................... 514/259

FOREIGN PATENT DOCUMENTS 0276825  8/1988  European Pat. Off. ............ 544/284
0276826  8/1988  European Pat. Off. ............ 544/284
225131   7/1985  German Democratic Rep. .
0258369 11/1987  Japan ................................... 544/284

OTHER PUBLICATIONS

McCarty, et al., "J.A.C.S.", vol. 82, No. 4, 1960, pp. 964-966.
Chaurasia, "Agr. Biol. Chem.", vol. 32, No. 6, 1968, pp. 711-714.
Choubey (I), "Agr. Biol. Chem.", vol. 33, No. 8, 1969, pp. 1213-1216.
Bhargava, et al. (I), "Chemical Abstracts", vol. 70, 1969, col. 87738p.
Murav'eva et al., "Chemical Abstracts", vol. 70, 1969, vol. 96748u.
Bhargava et al. (II), "Chemical Abstracts", vol. 72, 1970, Col. 31737m.
Bhargava, et al. (III), "Chemical Abstracts", vol. 77, 1972, Col. 483882.
Bhargava et al. (IV), "Chemical Abstracts", vol. 77, 1972, Col. 114250j.
Choubey (II), "Chemical Abstracts", vol. 77, 1972, Col. 88423p.
Bhargava et al. (IV), "Chemical Abstracts", vol. 80, 1974, Col. 146101g.
Bhargava et al. (VI), "Chemical Abstracts", vol. 85, 1976, Col. 85:5582f.
Chaurasia et al., "Chemical Abstracts", vol. 98, 1983, Col. 98:4512q.
"Chemical Abstracts", vol. 101, 1984, Col. 101:38470v.
Lakhan et al., "Chemical Abstracts", vol. 107, 1987, Col. 107:228515k.
Sato et al., "Chemical Abstracts", vol. 108, 1988, Col. 108:94581p.
J. Chem. Soc., vol. 82, p. 964, (1960).
J. Med. Chem., vol. 26, p. 218-222, (1983).
Chem. Abstr., vol. 83, 131542q, (1975).
Chem. Abstr., vol. 92, 146713f, (1980).
Chem. Abstr., vol. 102, 220825n, (1980).
Chem. Abstr., vol. 99, 158376f, (1983).
Chem. Abstr., vol. 89, 109345e, (1978).
Chem. Abstr., vol. 62, 14670g, (1965).
Chem. Abstr., vol. 57, 10284g, (1962).
Chem. Abstr., vol. 107, 36462u, (1987).
Chem. Abstr., vol. 106 102196t, (1987).

Primary Examiner—Frederick E. Waddell
Assistant Examiner—James H. Turnipseed
Attorney, Agent, or Firm—Abelman Frayne Rezac & Schwab

[57] ABSTRACT

4(3H)-Quinazolinone derivative of formula (I) are provided.

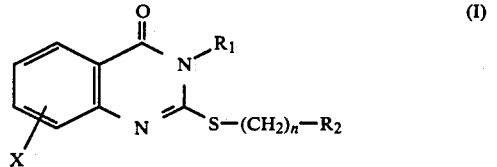

wherein $R_1$ is a hydrogen atom, a $C_1$–$C_6$ alkyl group, an aryl group, a substituted aryl group, or an aralkyl group; $R_2$ is a $C_1$–$C_6$ alkylamino group, a phenyl group, a substituted phenyl group, or a 5- or 6-membered heterocyclic group containing one or more N, O or S as a hetero atom or atoms, said heterocyclic group optionally being substituted or fused with a benzene ring; n is 1 or 2; or $R_2$ represents a geranyl group or a dipyridylmethyl group together with the group $-(CH_2)_n-$; and X is a hydrogen atom, a $C_1$–$C_6$ alkyl group or a halogen atom, and pharmaceutically acceptable acid addition salts thereof. They are useful as antiucler agents.

10 Claims, No Drawings

4(3H)-QUINAZOLINONE DERIVATIVES AND PHARMACEUTICAL COMPOSITIONS

CROSS REFERENCE TO RELATED APPLICATIONS

This application is a division of application Ser. No. 148,491, filed Jan. 26, 1988, now U.S. Pat. No. 4,861,780, granted Aug. 29, 1989.

FIELD OF THE INVENTION

The present invention relates to new 4(3H)-quinazolinone derivatives, processes for their preparation and their use as antiulcer agents.

BACKGROUND OF THE INVENTION

The agents used as the antiulcer drugs include $H_2$-receptor antagonists, anticholinergic agents, gastric mucosal protective agents and antacids, which are used depending upon the symptom of patients. These known agents, however, are of such drawbacks as generally weak activity and frequent occurrence of side effects.

For example, cimetidine, which is a $H_2$-receptor antagonist widely employed, is known to have side effects such as gynecomatism. Moreover, numbers of cases are reported about recurrence of ulcer after suspension of administration with cimetidine. Anticholinergic agents are known to have such side effects as suppression of gastric motility, corediastasis and thirst. Furthermore, they exhibit activity only for a limited period of time. Antacids are known to have frequent occurrence of such side effects as constipation.

As described above, known antiulcer agents were limitedly used in terms of manner of administration due to their side effects, and they have common drawback of exhibiting somewhat weak activity.

Some of the 4(3H)-quinazolinone derivatives are disclosed in J. Chem. Soc., vol. 82, p 964(1960); J. Med. Chem. 1983, 26, 218-222; Chem. Abstr., vol 83 131542q(1975) and Chem. Abstr., vol. 92 146713f(1980). Their uses are mentioned as ataractic agents in the first reference, as antiinflammatory agents in the second reference, as anthelmintics in the third reference and as radioprotectives in the fourth reference. However, there is no reference to the use of the 4(3H)-quinazolinone derivatives as antiulcer agents.

The present invention results from efforts to develop new 4(3H)-quinazolinone derivatives with more improved antiulcer effect.

DISCLOSURE OF THE INVENTION

According to the invention, there are provided 4(3H)-quinazolinone derivatives of formula (I)

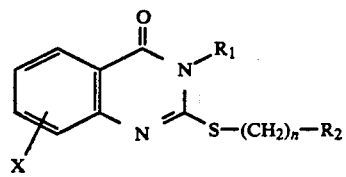

(I)

wherein $R_1$ is a hydrogen atom, a $C_1$-$C_6$ alkyl group, an aryl group, a substituted aryl group, or an aralkyl group; $R_2$ is a $C_1$-$C_6$ alkylamino group, a phenyl group, a substituted phenyl group, or a 5- or 6-membered heterocyclic group containing one or more N, O or S as a hetero atom or atoms, said heterocyclic group optionally being substituted or fused with a benzene ring; n is 1 or 2; or $R_2$ represents a geranyl group or a dipyridylmethyl group together with the group —$(CH_2)_n$—; and X is a hydrogen atom, a $C_1$-$C_6$ alkyl group or a halogen atom, and pharmaceutically acceptable acid addition salts thereof.

In the above formula (I), where $R_1$ is a $C_1$-$C_6$ alkyl group, it includes, for example, methyl, ethyl, propyl, isopropyl, butyl, isobutyl or pentyl group.

Where $R_1$ is an aryl group, it is preferably one having from 6 to 10 carbon atoms such as phenyl or naphthyl group.

Where $R_1$ is a substituted aryl group, the aryl group itself may be the same as one previously defined, and the substituent or substituents include, for example, a $C_1$-$C_6$ alkyl group, a $C_1$-$C_6$ alkoxy group and a halogen atom.

Where the substituent is a lower alkyl group, it may be the same as that defined for $R_1$.

Where the substituent is a $C_1$-$C_6$ alkoxy group, it includes, for example, methoxy, ethoxy, propoxy, isopropoxy, butoxy, isobutoxy, pentyloxy or hexyloxy group.

Where the substituent is a halogen atom, it includes, for example, fluorine, chlorine, bromine or iodine atom.

Where $R_1$ is an aralkyl group, it is preferably one having from 7 to 9 carbon atoms such as benzyl or phenethyl.

Where $R_2$ is a $C_1$-$C_6$ alkylamino group, it may be a di-$C_1$-$C_6$ alkylamino group such as diethylamino.

Where $R_2$ is a substituted phenyl group, the substituent or substituents include, for example, a $C_1$-$C_6$ alkylamino group such as di-$C_1$-$C_6$ alkylamino group (e.g. dimethylamino group) or a $C_1$-$C_6$ alkoxy group which may be the same as that defined for the substituent on the aryl group for $R_1$.

Thus, the substituted phenyl group includes, for example, a dimethylaminophenyl or a trimethoxyphenyl group.

Where $R_2$ is a 5- or 6-membered heterocyclic group containing one or more N, O or S as a hetero atom or atoms, said heterocyclic group optionally being substituted or fused with a benzene ring, the heterocyclic group itself may be, for example, furyl, thienyl, benzimidazolyl, pyridyl (e.g. 2-, 3-or 4-pyridyl), quinolyl or morpholino. The substituent or substituents on the heterocyclic group include, for example, a $C_1$-$C_6$ alkyl group or a $C_1$-$C_6$ alkoxy group as exemplified above.

Where X is a $C_1$-$C_6$ alkyl group, it may be the same as that defined for $R_1$.

Where X is a halogen atom, it may likewise be the same as that defined for the substituent on the aryl group of $R_1$.

Representative examples of the compounds represented by formula (I) are given hereinbelow.

3-Phenyl-2-(2-pyridylmethylthio)-4(3H)-quinazolinone,

5-Methyl-3-phenyl-2-(2-pyridylmethylthio)-4(3H)-quinazolinone,

7-Chloro-3-phenyl-2-(2-pyridylmethylthio)-4(3H)-quinazolinone, 3-(1-Naphthyl)-2-(2-pyridylmethylthio)-4(3H)-quinazolinone, 3-Phenyl-2-(2-quinolylmethylthio)-4(3H)-quinazolinone, 3-Phenethyl-2-(2-pyridylmethylthio)-4(3H)-quinazolinone, 2-(2-Furylmethylthio)-3-phenyl-4(3H)-quinazolinone, 3-Phenyl-2-(3,4,5-trimethoxybenzylthio)-4(3H)-quinazolinone,
3-Ethyl-2-(2-pyridylmethylthio)-4(3H)-quinazolinone,
3-Isobutyl-2-(2-pyridylmethylthio)-4(3H)-quinazolinone,
2-Geranylthio-3-phenyl-4(3H)-quinazolinone,
3-Phenyl-2-(4-pyridylmethylthio)-4(3H)-quinazolinone,
3-Phenyl-2-(2-thienylmethylthio)-4(3H)-quinazolinone,
2-(o-Dimethylaminobenzylthio)-3-phenyl-4(3H)-quinazolinone,
6-Methyl-3-phenyl-2-(2-pyridylmethylthio)-4(3H)-quinazolinone,
6-Bromo-2-(2-pyridylmethylthio)-3-phenyl-4(3H)-quinazolinone,
8-Methyl-3-phenyl-2-(2-pyridylmethylthio)-4(3H)-quinazolinone,
3-(2-Chlorophenyl)-2-(2-pyridylmethylthio)-4(3H)-quinazolinone,
6-Chloro-3-phenyl-2-(2-pyridylmethylthio)-4(3H)-quinazolinone,
2-[(4-Methoxy-5-methylpyridin-2-yl)methylthio]-3-phenyl-(4(3H)-quinazolinone,
3-(4-Methoxyphenyl)-2-(2-pyridylmethylthio)-4(3H)-quinazolinone,
3-(3-Methoxyphenyl)-2-(2-pyridylmethylthio)-4(3H)-quinazolinone,
3-(4-Methylphenyl)-2-(2-pyridylmethylthio)-4(3H)-quinazolinone,
2-[(4-Methoxy-3-methylpyridin-2-yl)methylthio]-3-(4-methoxyphenyl)-6-methyl-4(3H)-quinazoline,
3-(Phenyl)-2-[(4-methylpyridin-2-yl)methylthio]-4(3H)-quinazolino
2-[(4-methoxy-5-methylpyridin-2-yl)methylthio]-6-methyl-3-phenyl-4(3H)-quinazolinone,
3-Phenyl-2-(3-pyridylmethylthio)-4(3H)-quinazolinone,
3-Phenyl-2-(4-quinolylmethylthio)-4(3H)-quinazolinone,
2-[Di(2-pyridyl)methylthio]-3-phenyl-4(3H)-quinazolinone,
3-(4-Methylphenyl)-2-(4-pyridylmethylthio)-4(3H)-quinazolinone, and
8-Methyl-2-(4-pyridylmethylthio)-4(3H)-quinazolinone.

The compounds of formula (I) according to the invention can be prepared by reacting a compound of formula (II) with a compound of formula (III) in the presence of a base.

<chemical structure: (II) quinazolinone with N-R1, SH, and X substituents; (III) R2—(CH2)n—Y>

In the above formulas, Y is a halogen atom, and R1, R2, n and X have the same meanings as defined above.

The reaction of the compound (II) with the compound (III) is advantageously carried out in the presence of a base. The nature of the base used is not critical and it may include inorganic bases such as sodium hydroxide, potassium hydroxide or ammonium hydroxide, organic bases such as diethylamine, triethylamine or pyridine, and alkali metal alkoxides such as sodium methoxide, potassium methoxide, sodium ethoxide or potassium t-butoxide.

In performing the reaction, the compound (III) may be used in the propotion of from 0.5 to 5 moles, per mole of the compound (II). Generally, however, it is preferable that the compound (III) is used in equal or excess amount to the compound (II). For example, the compound (III) is preferably used in the proportion of from 1 to 3 moles per mole of the compound (II).

The reaction is normally carried out in a solvent, the nature of which is not critical, and it may be, for example, water, lower alcohols such as methanol, ethanol or butanol; polar solvents such as dimethyl sulfoxide or dimethylformamide; ethers such as diethyl ether, tetrahydrofuran or dioxane; esters such as ethyl acetate; ketones such as acetone; or mixtures of water with any of the solvents described above.

Normally, the reaction is performed at temperatures of from 0° C. to 150° C., preferably from room temperature to the reflux temperature of the solvent used.

Representative examples of the compounds represented by formula (II) are given hereinbelow.
2-Mercapto-3-phenyl-4(3H)-quinazolinone,
2-Mercapto-5-methyl-3-phenyl-4(3H)-quinazolinone,
7-Chloro-2-mercapto-3-phenyl-4(3H)-quinazolinone,
3-Ethyl-2-mercapto-4(3H)-quinazolinone,
2-Mercapto-3-naphthyl-4(3H)-quinazolinone,
3-Isobutyl-2-mercapto-4(3H)-quinazolinone,
2-Mercapto-3-phenethyl-4(3H)-quinazolinone,
2-Mercapto-4(3H)-quinazolinone,
3-(2-Chlorophenyl)-2-mercapto-4(3H)-quinazolinone,
2-Mercapto-3-(4-methylphenyl)-4(3H)-quinazolinone,
2-Mercapto-3-(4-methoxyphenyl)-4(3H)-quinazolinone,
2-Mercapto-3-(3-methoxyphenyl)-4(3H)-quinazolinone,
2-Mercapto-6-methyl-3-phenyl-4(3H)-quinazolinone,
6-Chloro-2-mercapto-3-phenyl-4(3H)-quinazolinone,
6-Bromo-2-mercapto-3-phenyl-4(3H)-quinazolinone,
2-Mercapto-8-methyl-3-phenyl-4(3H)-quinazolinone, and
2-Mercapto-3-(4-methoxyphenyl)-6-methyl-4(3H)-quinazolinone, Representative examples of the compounds represented by formula (III) are given hereinbelow.
2-Chloromethylpyridine,
3-Chloromethylpyridine,
4-Chloromethylpyridine,
2-Chloromethylquinoline,
2-Chloromethylbenzimidazole,
2-Chloromethylfuran,
2-Bromomethylthiophene,
Benzyl chloride,
3,4,5-Trimethoxybenzyl chloride,
o-Dimethylaminobenzyl chloride,
Diethylaminoethyl chloride,
Geranyl bromide,
N-(2-Chloroethyl)morpholine,
2-Chloromethyl-4-methylpyridine,
2-Chloromethyl-4-methoxy-5-methylpyridine,
2-Chloromethyl-4-methoxy-3-methylpyridine, and
Di(2-pyridyl)methyl chloride.

The compounds of formula (I) may be converted, if desired, to pharmaceutically acceptable acid addition salts thereof, and these salts are embraced within the scope of this invention.

Concrete examples of addition salts include the salts of the compounds with inorganic acids such as hydrochloric acid, hydrobromic acid, hydroiodic acid, nitric acid, sulfuric acid or phosphoric acid, and organic acids such as formic acid, acetic acid, propionic acid, butyric acid. maleic acid, fumaric acid, malonic acid, malic acid, citric acid, tartaric acid or oxalic acid.

The compounds of formula (I) and pharmaceutically acceptable acid addition salts thereof are of prominent antiulcer activity.

Thus, the present invention also relates to pharmaceutical compositions which comprise as an active ingredient the compounds of formula (I) or pharmaceutically acceptable acid addition salts thereof.

The pharmaceutical compositions of the invention may be formulated into various forms which are commonly used in the art and which are administered orally or parenterally. For example, they may be formulated into tablets, capsules, suppositories, troches, syrups, creams, ointments, granules, powders, injectable solutions or suspensions. Alternatively, they may be formulated into double or multiple layer tablets, together with other active principles. Furthermore, they may be formulated into coated tablets such as sugar-coated tablets, enteric-coated tablets and film-coated tablets.

In order to obtain solid preparations, the compounds of this invention are mixed with such conventional diluents or fillers as lactose, refined sugar, crystalline cellulose, corn starch, calcium phosphate, sorbitol, glycine, carboxymethyl-cellulose, gum arabic, polyvinylpyrrolidone, hydroxypropylcellulose, glycerol, polyethylene glycol, stearic acid, magnesium stearate or talc.

In order to obtain semi-solid preparations, the compounds of this invention are mixed with such additives as plant wax, synthetic wax or fats.

In order to obtain liquid preparations, the compounds of this invention are mixed with such diluents or additives as sodium chloride, sorbitol, glycerol, olive oil, almond oil, propylene glycol or ethanol.

The compounds of the invention may normally be contained in a preparation in an amount of from 0.1% to 100% by weight, more suitably in an amount of from 1% to 50% by weight in the case of preparations for oral administration and from 0.2% to 20% by weight in the case of injectable preparations.

There is no particular limitation as to the method of administration and the dosage of the antiulcer agents according to the invention. They are chosen, depending on the form of preparation, age of patients, sex, degree of symptom, etc. Normally, however, the dosage will be in the range of from 10 to 1,000 mg per day.

The pharmaceutical composition of the invention may be administered in conjunction with one or more other active principles such as antacids, non-steroid anti-inflammatory agents or other types of antiulcer agents.

BEST MODE OF CARRYING OUT THE INVENTION

The invention will be explained in more detail by the following Examples, which are to be understood not to limit the scope of this invention.

EXAMPLE 1

3-Phenyl-2-(2-pyridylmethylthio)-4-(3H)-quinazolinone 6.1 ml Of 28% methanolic solution of sodium methoxide and 2.46 g of 2-chloromethylpyridine hydrochloride were added to a solution of 3.62 g of 2-mercapto-3-phenyl-4(3H)-quinazolinone in 100 ml of methanol, and the stirring was continued at room temperature for 2.5 hours. About 50 ml of water were added to the reaction solution and crystals precipitated were collected by filtration and recrystallized from ethyl acetate to give 2.45 g of the title compound.
White crystals
M.P. 182.3–183.3° C.
NMR(CDCl$_3$,$\delta$):
   4.56(2H,s), 7.10–7.79(11H,m), 8.25(1H,d), 8.52(1H,d)
IR(nujol,cm$^{-1}$): 1680, 1610, 1590

EXAMPLE 2

Following the procedure described in Example 1, the following compounds (a) to (i) were prepared.

(a) 2-Benzylthio-3-phenyl-4(3H)-quinazolinone

The title compound was prepared in a yield of 52%, using benzyl chloride in place of 2-chloromethylpyridine hydrochloride.
White crystals (from ethyl acetate)
M.P. 168.9–170.8° C.
NMR(CDCl$_3$,$\delta$):
   4.41(2H,s), 7.17–7.56(11H,m), 7.62–7.80(2H,m), 8.24(1H,d)
IR(nujol,cm$^{-1}$): 1680, 1610, 1575, 1550

(b) 2-(2-Pyridylmethylthio)-4(3H)-quinazolinone

The title compound was prepared in a yield of 30.4%, using 2-mercapto-4(3H)-quinazolinone in place of 2-mercapto-3-phenyl-4(3H)-quinazolinone.
White crystals (from acetone)
M.P. 186.7–195.5° C.
NMR(CDCl$_3$,+DMSO$^{d-6}$,$\delta$):
   4.62(2H,s), 7.17–7.76(6H,m), 8.15(1H,d), 8.56(1H,d)
IR(nujol,cm$^{-1}$): 3200, 1690, 1590, 1550

(c) 5-Methyl-3-phenyl-2-(2-pyridylmethylthio)-4(3H)-quinazolinone

The title compound was prepared in a yield of 64.9%, using 2-mercapto-5-methyl-3-phenyl-4(3H)-quinazolinone in place of 2-mercapto-3-phenyl-4(3H)-quinazolinone.
White needles (from ethyl acetate/diisopropyl ether)
M.P. 172.6–174.0° C.
NMR(CDCl$_3$,$\delta$):
   2.80(2H,s), 4.54(2H,s), 7.09–7.66(11H,m), 8.51(1H,d)
IR(nujol,cm$^{-1}$): 1685, 1600, 1590, 1550

(d) 7-Chloro-3-phenyl-2-(2-pyridylmethylthio)-4(3H)-quinazolinone

The title compound was prepared in a yield of 71.4%, using 7-chloro-2-mercapto-3-phenyl-4(3H)-quinazolinone in place of 2-mercapto-3-phenyl-4(3H)-quinazolinone.
White needles (from ethyl acetate)
M.P. 184.1–185.7° C.
NMR(CDCl$_3$,$\delta$):
   4.53(2H,s), 7.10–7.69(10H,m), 8.16(1H,d), 8.53(1H,d)
IR(nujol,cm$^{-1}$, 1690, 1600, 1590, 1570

(e) 3-(1-Naphthyl)-2-(2-pyridylmethylthio)-4(3H)-quinazolinone

The title compound was prepared in a yield of 58.1%, using 2-mercapto-3-(1-naphthyl)-4(3H)-quinazolinone in place of 2-mercapto-3-phenyl-4(3H)-quinazolinone.
White crystals (from acetone)
M.P. 197.4–201.3° C.
NMR(CDCl$_3$,$\delta$):
   4.43(1H,d,J=12Hz), 4.59(1H,d,J=12Hz), 7.08–8.05(13H,m), 8.27(1H,d), 8.47(1H,d)
IR(nujol,cm$^{-1}$): 1680, 1600, 1590, 1580

(f) 3-Phenyl-2-(2-quinolylmethylthio)-4(3H)-quinazolinone

The title compound was prepared in a yield of 39%, using 2-chloromethylquinoline hydrochloride in place of 2-chloromethylpyridine hydrochloride.

White crystals (from ethyl acetate)
M.P. 204.9–207.1° C. (dec)
NMR(CDCl$_3$,δ):
  4.77(2H,s), 7.38–7.82(12H,m), 7.98–8.13(2H,m), 8.30(1H,d)
IR(nujol,cm$^{-1}$): 1675, 1605

(g) 3-Phenethyl-2-(2-pyridylmethylthio)-4(3H)-quinazolinone

The title compound was prepared in a yield of 48.3%, using 2-mercapto-3-phenethyl-4(3H)-quinazolinone in place of 2-mercapto-3-phenyl-4(3H)-quinazoline.
White needles (from ethyl acetate)
M.P. 120.6–122.4° C.
NMR(CDCl$_3$,δ)
  2.99–3.12(2H,m), 4.25–4.38(2H,m), 4.71(2H,s), 7.15–7.79(11H,m), 8.23(1H,d), 8.60(1H,d)
IR(nujol,cm$^{-1}$): 1680, 1610, 1550

(h) 2-(2-Furylmethylthio)-3-phenyl-4(3H)-quinazolinone

The title compound was prepared in a yield of 14.6%, using 2-chloromethylfuran in place of 2-chloromethylpyridine hydrochloride.
White crystals (from acetone/diisopropyl ether)
M.P. 155.3–157.3° C.
NMR(CDCl$_3$,δ)
  4.48(2H,s), 6.25–6.36(2H,m), 7.26–7.82(9H,m), 8.25(1H,d)
IR(nujol,cm$^{-1}$): 1685, 1610, 1550

(i) 3-Phenyl-2-(3,4,5-trimethoxybenzylthio)-4(3H)-quinazolinone

The title compound was prepared in a yield of 25%, using 3,4,5-trimethoxybenzyl chloride in place of 2-chloromethylpyridine hydrochloride.
White crystals (from ethyl acetate)
M.P. 151.0–152,8° C.
NMR(CDCl$_3$,δ):
  3.80(3H,s), 3.83(6H,s), 4.38(2H,s), 6.64(2H,s), 7.28–7.81(8H,m), 8.26(1H,d)
IR(nujol,cm$^{-1}$): 1690, 1610, 1590, 1580, 1555

EXAMPLE 3

3-Ethyl-2-(2-pyridylmethylthio)-4(3H)-quinazolinone 7.0 ml of 28% methanolic solution of sodium methoxide and 2.82 g of 2-chloromethylpyridine hydrochloride were added, in turn, to a solution of 3.56 g of 3-ethyl-2-mercapto-4(3H)-quinazolinone in 50 ml of methanol, and the stirring was continued at room temperature for 4 hours. The reaction solution was poured into about 300 ml of water and extracted with chloroform. The extract was dried over sodium sulfate and the solvent was distilled off under reduced pressure. The residue was recrystallized from a mixture of ethyl acetate and diisopropyl ether, to give 2.47 g of the title compound.
White crystals
M.P. 110.1–111.1° C.
NMR(CDCl$_3$,δ):
  1.36(3H,t), 4.26(2H,q), 4.67(2H,s), 7.14–7.74(6H,m), 8.21(1H,d), 8.59(1H,d)
IR(nujol,cm$^{-1}$): 1675, 1610, 1550

EXAMPLE 4

3-Isobutyl-2-(2-pyridylmethylthio)-4(3H)-quinazolinone 5.4 ml Of 28% methanolic solution of sodium methoxide and 2.3 g of 2-chloromethylpyridine hydrochloride were added, in turn, to a solution of 3.0 g 3-isobutyl-2-mercapto-4(3H)-quinazolinone in 50 ml of methanol, and the stirring was continued at room temperature for 15 hours. The reaction solution was poured into about 300 ml of water and extracted with chloroform. The extract was dried over sodium sulfate and the solvent was distilled off under reduced pressure. The residue was purified by silica column chromatography eluted with 10% ethyl acetate in chloroform. The fraction obtained from the eluent was further purified by crystallization from a mixture of ethyl acetate and diisopropylether to give 1.92 g of the title compound.
White crystals
M.P. 91.7–93.2° C.
NMR(CDCl$_3$,δ):
  0.96(6H,d), 2.22–2.41(1H,m), 4.02(2H,d), 4.68(2H,s), 7.13–7.76(6H,m), 8.22(1H,d), 8.59(1H,d)
IR(nujol,cm$^{-1}$): 1665, 1610, 1595, 1540

EXAMPLE 5

Following the procedure of Example 4, the following compounds (a) to (g) were prepared.

(a) 2-(2-Diethylaminoethylthio)-3-phenyl-4(3H)-quinazolinone

The title compound was prepared in a yield of 32.7%, using 2-mercapto-3-phenyl-4(3H)-quinazolinone in place of 3-isobutyl-2-mercapto-4(3H)-quinazoline and β-diethylaminoethyl chloride hydrochloride in place of 2-chloromethylpyridine hydrochloride.
White crystals
M.P. 84.8–86.8° C.
NMR(CDCl$_3$,δ):
  1.08(6H,t), 2.62(4H,q), 2.72–2.82(2H,m), 3.18–3.28(2H,m), 7.25–7.78(8H,m), 8.25(1H,d)
IR(nujol,cm$^{-1}$): 1690, 1610, 1575, 1550

(b) 2-Geranylthio-3-phenyl-4(3H)-quinazolinone

The title compound was prepared in a yield of 57.6%, using 2-mercapto-3-phenyl-4(3H)-quinazolinone in place of 3-isobutyl-2-mercapto-4(3H)-quinazolinone and geranyl bromide in place of 2-chloromethylpyridine hydrochloride.
Transparent, pale yellow oily product
NMR(CDCl$_3$,δ):
  1.50–1.74(9H,m), 1.90–2.13(4H,m), 3.84(2H,d), 5.02(1H,t), 5.28(1H,t), 7.27–7.78(8H,m), 8.24(1H,d)
IR(neat,cm$^{-1}$): 1690, 1610, 1575, 1550

(c) 2-(2-Benzimidazolylmethylthio)-3-phenyl-4(3H)-quinazolinone

The title compound was prepared in a yield of 39.3%, using 2-mercapto-3-phenyl-4(3H)-quinazolinone in place of 3- isobutyl-2-mercapto-4(3H)-quinazolinone and 2-chloromethylbenzimidazole in place of 2-chloromethylpyridine hydrochloride.
White crystals (from ethyl acetate)
M.P. 149.0–151.4° C.
NMR(CDCl$_3$,δ):
  4.57(2H,s), 7.15–7.87(12H,m), 8.28(1H,d)
IR(nujol,cm$^{-1}$): 1685, 1600, 1570, 1550

(d) 2-(2-Morpholinoethylthio)-3-phenyl-4(3H)-quinazolinone

The title compound was prepared in a yield of 49.8%, using 2-mercapto-3-phenyl-4(3H)-quinazolinone in place of 3- isobutyl-2-mercapto-4(3H)-quinazolinone and N-(2-chloroethyl)morpholine in place of 2-chloromethylpyridine hydrochloride.
Transparent, colorless oily product
NMR(CDCl$_3$,δ):
  2.43–2.76(6H,m), 3.24–3.43(2H,m), 3.65–3.75(4H,m), 7.24–7.63(7H,m), 7.75(1H,t), 8.24(1H,d)
IR(neat,cm$^{-1}$): 1685, 1620, 1590, 1545

(e) 3-Phenyl-2-(4-pyridylmethylthio)-4(3H)-quinazolinone

The title compound was prepared in a yield of 20.7%, using 2-mercapto-3-phenyl-4(3H)-quinazolinone in place of 3- isobutyl-2-mercapto-4(3H)-quinazolinone.
White crystals (from ethyl acetate)
M.P. 180.2-181.9° C. (dec)
NMR(CDCl$_3$,δ);
    4.36(2H,s), 7.25-7.81(10H,m), 8.23(1H,d), 8.49-8.55(2H,m)
IR(nujol,cm$^{-1}$): 1685, 1600, 1570, 1550

(f) 3-Phenyl-2-(2-thienylmethylthio)-4(3H)-quinazolinone

The title compound was prepared in a yield of 37.4%, using 2-mercapto-3-phenyl-4(3H)-quinazolinone in place of 3- isobutyl-2-mercapto-4(3H)-quinazolinone and 2-bromomethylthiophene in place of 2-chloromethylpyridine hydrochloride.
Pale yellow crystals (from ethyl acetate/isopropyl ether)
M.P. 162.3° C.
NMR(CDCl$_3$,δ):
    4.63(2H,s), 6.85-6.93(1H,m), 6.99-7.04(1H,m), 7.13-7.21(1H,m), 7.25-7.83(8H,m), 8.25(1H,d)
IR(nujol,cm$^{-1}$): 1695, 1610, 1555

(g) 2-(o-Dimethylaminobenzylthio)-3-phenyl-4(3H)-quinazolinone

The title compound was prepared in a yield of 26.9%, using 2-mercapto-3-phenyl-4(3H)-quinazolinone in place of 3- isobutyl-2-mercapto-4(3H)-quinazolinone and 2-chloromethyl-N,N-dimethylaniline in place of 2-choromethylpyridine hydrochloride.
Transparent, colorless oily product
NMR(CDCl$_3$,δ):
    2.65(6H,s), 4,58(2H,s), 6.94-7.79(12H,m), 8.24(1H,d)
IR(CHCl$_3$,cm$^{-1}$): 1680, 1610, 1575, 1550

EXAMPLE 6

6-Methyl-3-phenyl-2-(2-pyridylmethylthio)-4(3H)-quinazolinone 9.5 ml Of 28% methanolic solution of sodium methoxide were added to a solution of 6.0 g of 2-mercapto-6-methyl-3- phenyl-4(3H)-quinazolinone and 4.0 g of 2-chloromethylpyridine hydrochloride in methanol, the mixture was stirred at room temperature for 2 hours and allowed to stand overnight. Crystals precipitated were collected by filtration and recrystallized from ethyl acetate to give 4.2 g (52.2%) of the title compound.
White crystals
M.P. 167.2-169.2° C.
NMR(CDCl$_3$,δ):
    2.48(3H,s), 4.55(2H,s), 7.10-7.20(1H,m), 7.25-7.36(2H,m), 7.45-7.69(7H,m), 8.02(1H,s), 8.53(1H,d)
IR(nujol,cm$^{-1}$): 1685

EXAMPLE 7

Following the procedure of Example 6, the following compounds (a) to (i) were prepared.

(a) 6-Bromo-2-(2-pyridylmethylthio)-3-phenyl-4(3H)-quinazolinone

The title compound was prepared in a yield of 66.7%, using 6-bromo-2-mercapto-3-phenyl-4(3H)-quinazolinone in place of 2-mercapto-6-methyl-3-phenyl-4(3H)-quinazolinone.
White crystals (from ethyl acetate)
M.P. 172.3-173.8° C.
NMR(CDCl$_3$,δ):
    4.54(2H,s), 7.10-7.20(1H,m), 7.23-7.35(2H,m), 7.43-7.69(6H,m), 7.81(1H,d), 8.35(1H,d), 8.52(1H,d)
IR(nujol,cm$^{-1}$): 1690

(b) 8-Methyl-3-phenyl-2-(2-pyridylmethylthio)-4(3H)-quinazolinone

The title compound was prepared in a yield of 28%, using 2-mercapto-8-methyl-3-phenyl-4(3H)-quinazolinone in place of 2-mercapto-6-methyl-3-phenyl-4(3H)-quinazolinone.
White crystals (from ethyl acetate)
M.P. 165.0-166.4° C.
NMR(CDCl$_3$,δ):
    2.60(3H,s), 4.60(2H,s), 7.11-7.21(1H,m), 7.29-7.68(9H,m), 8.10(1H,d), 8.52(1H,d)
IR (nujol,cm$^{-1}$): 1690, 1595

(c) 3-(2-Chlorophenyl)-2-(2-pyridylmethylthio)-4(3H)-quinazolinone

The title compound was prepared in a yield of 57.1%, using 3-(2-chlorophenyl)-2-mercapto-4(3H)-quinazolinone in place of 2-mercapto-6-methyl-3-phenyl-4(3H)-quinazolinone.
White crystals (from ethyl acetate)
M.P. 173.8-178.3° C.
NMR(CDCl$_3$,δ):
    4.59(2H,s), 7.10-7.20(1H,m), 7.34-7.82(9H,m), 8.25(1H,d), 8.52(1H,d)
IR(nujol,cm$^{-1}$): 1690, 1615

(d) 6-Chloro-3-phenyl-2-(2-pyridylmethylthio)-4(3H)-quinazolinone

The title compound was prepared in a yield of 65.2%, using 6-chloro-2-mercapto-3-phenyl-4(3H)-quinazolinone in place of 2-mercapto-6-methyl-3-phenyl-4(3H)-quinazolinone.
White crystals (from ethyl acetate)
M.P. 174.9-176.5° C.
NMR(CDCl$_3$,δ):
    4.55(2H,s), 7.11-7.21(1H,m), 7.24-7.36(2H,m), 7.43-7.74(7H,m), 8.19(1H,d), 8.52(1H,d)
IR(nujol, cm$^{-1}$): 1690

(e) 2-[(4-Methoxy-5-methylpyridin-2-yl)methylthio]-3-phenyl4(3H)-quinazolinone

The title compound was prepared in a yield of 22.5%, using 2-mercapto-3-phenyl-4(3H)-quinazolinone in place of 2- mercapto-6-methyl-3-phenyl-4(3H)-quinazolinone and 2-chloromethyl-4-methoxy-5-methylpyridine in place of 2-chloromethylpyridine hydrochloride.
White crystals (from ethyl acetate)
M.P. 175.5-178.0° C.
NMR(CDCl$_3$,δ):
    2.12(3H,s), 3.85(3H,s), 3.85(3H,s), 4.50(2H,s), 7.03(1H,s), 7.25-7.82(8H,m), 8.13(1H,s), 8.25(1H,d)
IR(nujol,cm$^{-1}$): 1685, 1605

(f) 3-(4-Methoxyphenyl)-2-(2-pyridylmethylthio)-4(3H)-quinazolinone

The title compound was prepared in a yield of 58.9%, using 2-mercapto-3-(4-methoxyphenyl)-4(3H)-quinazolinone in place of 2-mercapto-6-methyl-3-phenyl-4(3H)-quinazolinone.
White crystals (from chloroform/isopropyl ether)
M.P. 195.4° C.
NMR(CDCl$_3$,δ):
    3.85(3H,s), 4.56(2H,s), 7.01(2H,d), 7.10-7.29(3H, m), 7.34-7.80(5H,m), 8.24(1H,d), 8.52(1H,d)
IR(nujol, cm$^{-1}$): 1680, 1610

(g) 3-(3-Methoxyphenyl)-2-(2-pyridylmethylthio)-4(3H)-quinazolinone

The title compound was prepared in a yield of 67.9%, using 3-(3-methoxyphenyl)-2-mercapto-4(3H)-quinazolinone in place of 2-mercapto-6-methyl-3-phenyl-4(3H)-quinazolinone.

White crystals (from ethyl acetate)
M.P. 178.5–180.3° C.
NMR(CDCl$_3$,δ):
  3.82(3H,s), 4.56(2H,s), 6.81–6.95(2H,m), 7.04(1H,d), 7.12–7.20(1H,m), 7.34–7.80(6H,m), 8.25(1H,d), 8.53(1H,d)
IR(nujol, cm$^{-1}$): 1690, 1610

(h) 3-(4-Methylphenyl)-2-(2-pyridylmethylthio)-4(3H)-quinazolinone

The title compound was prepared in a yield of 45.5%, using 2-mercapto-3-(4-methylphenyl)-4(3H)-quinazolinone in place of 2-mercapto-6-methyl-3-phenyl-4(3H)-quinazolinone.

White crystals (from chloroform/isopropyl ether)
M.P. 169.3–171.1° C.
NMR(CDCl$_3$,δ):
  2.42(3H,s), 4.55(2H,s), 7.10–7.81(10H,m), 8.23(1H,d), 8.51(1H,d)
IR(nujol, cm$^{-1}$): 1685, 1610

(i) 2-[(4-Methoxy-3-methylpyridin-2-yl)methylthio]-3-(4-methoxyphenyl)-6-methyl-4(3H)-quinazolinone The title compound was prepared in a yield of 51.6%, using 2-mercapto-3-(4-methoxyphenyl)-6-methyl-4(3H)-quinazolinone in place of 2-mercapto-6-methyl-3-phenyl-4(3H)-quinazolinone and 2-chloromethyl-4-methoxy-3-methylpyridine hydrochloride in place of 2-chloromethylpyridine hydrochloride.

White crystals (from chloroform/isopropyl ether)
M.P. 199.9–203.8° C.
NMR(CDCl$_3$,δ):
  2.27(3H,s), 2.48(3H,s), 3.83(6H,s), 4.60(2H,s), 6.65(1H,d), 6.99(2H,d), 7.23(2H,d), 7.53–7.57(2H,m), 8.02(1H,s), 8.26(1H,d)
IR(nujol, cm$^{-1}$): 1680, 1610

EXAMPLE 8

3-Phenyl-2-[(4-methylpyridin-2-yl)methylthio]-4(3H)-quinazolinone 8.7 ml of 28% methanolic solution of sodium methoxide were added to a solution of 5.0 g of 2-mercapto-3-phenyl-4(3H)-quinazolinone and 4.0 g of 2-chloromethyl-4-methylpyridine hydrochloride in methanol, and the stirring was continued at room temperature for 5 hours. The reaction solution was poured into water and extracted with chloroform. The chloroform layer was washed with an aqueous solution of sodium carbonate and dried over sodium sulfate. The solvent was distilled off under reduced pressure and the residue was purified by silica gel column chromatography. The fraction eluted with 8% ethyl acetate in chloroform was collected and crystallized from ethyl acetate to give 2.17 g (30.7%) of the title compound.

White crystals
M.P. 144.6–150.1° C.
NMR(CDCl$_3$,δ):
  2.32(3H,s), 4.53(2H,s), 6.98(1H,d), 7.26–7.80(9H,m), 8.25(1H,d), 8.38(1H,d)
IR(nujol,cm$^{-1}$): 1695, 1660

EXAMPLE 9

Following the procedure of Example 8, the following compounds (a) to (f) were prepared.

(a) 2-[(4-Methoxy-5-methylpyridin-2-yl)methylthio]-6-methyl-3-phenyl-4(3H)-quinazolinone The title compound was prepared in a yield of 32.9%, using 2-mercapto-6-methyl-3-phenyl-4(3H)-quinazolinone in place of 2-mercapto-3-phenyl-4(3H)-quinazolinone and 2-chloromethyl-4-methoxy-5-methylpyridine in place of 2chloromethyl-4-methylpyridine hydrochloride.

White crystals (from ethyl acetate)
M.P. 166.3–169.2° C.
NMR(CDCl$_3$,δ):
  2.12(3H,s), 2.48(3H,s), 3.85(3H,s), 4.49(2H,s), 7.03(1H,s), 7.23–7.37(2H,m), 7.44–7.66(5H,m), 8.03(1H,s), 8.13(1H,s)
IR(nujol, cm$^{-1}$): 1680, 1600

(b) 3-Phenyl-2-(3-pyridylmethylthio)-4(3H)-quinazolinone

The title compound was prepared in a yield of 27.9%, using 3-chloromethylpyridine in place of 2-chloromethyl-4-methylpyridine hydrochloride.

White crystals (from chloroform/isopropyl ether)
NMR(CDCl$_3$,δ):
  4.39(2H,s), 7.19–7.87(10H,m), 8.23(1H,d), 8.48(1H,d), 8.70(1H,d)
IR(nujol, cm$^{-1}$): 1690, 1610

(c) 3-Phenyl-2-(4-quinolylmethylthio)-4(3H)-quinazolinone

The title compound was prepared in a yield of 40.8%, using 4-chloromethylquinoline in place of 2-chloromethyl-4-methylpyridine hydrochloride.

White crystals (from ethyl acetate)
M.P. 175.4–179.0° C.
NMR(CDCl$_3$,δ):
  4.89(2H,s), 7.23–7.83(11H,m), 8.11(2H,t), 8.26(1H,d), 8.82(1H,d)
IR(nujol, cm$^{-1}$): 1690, 1610, 1595

(d) 2-[Di(2-pyridyl)methylthio]-3-phenyl-4(3H)-quinazolinone

The title compound was prepared in a yield of 8.3%, using di(2-pyridyl)methyl chloride in place of 2-chloromethyl-4methylpyridine hydrochloride.

Yellow crystals (from ethyl acetate)
M.P. 208.8–212.0° C. (dec)
NMR(CDCl$_3$,δ):
  6.57(1H,s), 7.06–7.17(2H,m), 7.25–7.80(12H,m), 8.18(1H,d), 8.53(2H,d)
IR(nujol, cm$^{-1}$): 1690

(e) 3-(4-Methylphenyl)-2-(4-pyridylmethylthio)-4(3H)-quinazolinone

The title compound was prepared in a yield of 60.8%, using 2-mercapto-3-(4-methylphenyl)-4(3H)-quinazolinone in place of 2-mercapto-3-phenyl-4(3H)-quinazolinone and 4-chloromethylpyridine hydrochloride in place of 2-chloromethyl-4methylpyridine hydrochloride.

White crystals (from ethyl acetate)
M.P. 157.0–158.9° C.
NMR(CDCl$_3$,δ):
  2.45(3H,s), 4.36(2H,s), 7.12–7.48(7H,m), 7.61(1H,d), 7.75(1H,t), 8.24(1H,d), 8.53(2H,d)
IR(nujol, cm$^{-1}$): 1610, 1600

(f) 8-Methyl-2-(4-pyridylmethylthio)-4(3H)-quinazolinone

The title compound was prepared in a yield of 44.0%, using 2-mercapto-8-methyl-4(3H)-quinazolinone in place of 2-mercapto-3-phenyl-4(3H)-quinazolinoe and 4-chloromethylpyridine hydrochloride in place of 2-chloromethyl-4methylpyridine hydrochloride.
White crystals (from ethyl acetate)
M.P. 204.1-207.7° C.
NMR(CDCl$_3$,δ):
2.56(3H,s), 4.42(2H,s), 7.24–7.65(9H,m), 8.10(1H,d), 8.54(2H,d)
IR(nujol, cm$^{-1}$): 1690, 1600

EXAMPLE 10

The antiulcer activity of the compounds of this invention was determined by the following method.

Four-week-old ddY series male mice were used as the test animals after they were fasted for 24 hours. Each test compound suspended in a 1% gum arabic solution was administerd to the stomach of each mouse at a dose of 100 mg/kg, and then, after 30 minutes, 20 mg/kg of indomethacin was administered orally. Four hours after the administration of indomethacin, the stomach of mouse was extirpated and the length of ulcers was measured. Then, the ulcer index was determined by the total sum of the scores as calculated in Table 1.

TABLE 1

| Length of ulcer | 0.5 mm< | 1 mm< | 2 mm< | 3 mm< |
|---|---|---|---|---|
| Score | 0.5 | 1 | 2 | 3 |

The mean ulcer index of each group was calculated and the suppression rate against the control group in terms of difference in the mean ulcer index was determined. The results are shown in Table 2.

TABLE 2

| Compound tested | Suppression rate of indomethacin induced ulcer, 100 mg/kg, p.o. |
|---|---|
| 3-Phenethyl-2-(2-pyridylmethylthio)-4(3H)-quinazolinone | 60 |
| 3-Ethyl-2-(2-pyridylmethylthio)-4(3H)-quinazolinone | 96 |
| 2-(2-Diethylaminoethylthio)-3-phenyl-4(3H)-quinazolinone | 45 |
| 2-(2-Benzimidazolylmethylthio)-3-phenyl-4(3H)-quinazolinone | 81 |
| 6-Methyl-3-phenyl-2-(2-pyridylmethylthio)-4(3H)-quinazolinone | 38 |
| 2-[(4-Methoxy-3-methylpyridin-2-yl)-methylthio]-3-(4-methoxyphenyl)-6-methyl-3-phenyl-4(3H)-quinazolinone | 49 |
| 2-[(4-Methoxy-5-methylpyridin-2-yl)-methylthio]-6-methyl-3-phenyl-4(3H)-quinazolinone | 44 |
| 3-Phenyl-2-(3-pyridylmethylthio)-4(3H)-quinazolinone | 63 |
| Cimetidine (Control) | 40 |

As shown in Table 2, it is vident that the compounds of the invention possess the antiulcer activity comparable to or superior to that of cimetidine.

The compounds of this invention have generally low toxicity.

For example, LD$_{50}$ value(P.O.) of 3-ethyl-2-(2-pyridylmethylthio)-4(3H)-quinazolinone is higher than 3,000 mg/kg. The reversion test on the compound reveals the negative result.

Examples in which the compounds of present invention are formulated into various preparations are illustrated below.

PREPARATION 1

Tablet 50 mg Of 3-ethyl-2-(2-pyridylmethylthio)-4(3H)-quinazolinone, 77 mg of lactose, 15 mg of crystalline cellulose, 7 mg of corn starch and 1 mg of magnesium stearate (each per tablet) were thoroughly mixed, and then the mixture was tableted with a rotary tableting machine into a tablet of 7 mm diameter, weight 150 mg.

PREPARATION 2

Granule 50 mg Of 3-ethyl-2-(2-pyridylmethylthio)-4(3H)-quinazolinone, 230 mg of lactose, 110 mg of corn starch and 100 mg of crystalline cellulose were thoroughly mixed. Meanwhile, 10 mg of hydroxypropylcellulose were dissolved in 90 mg of ethanol and the solution was added to the previously prepared mixture. The whole mixture was kneaded and granulated. The granules were air-dried at 50° C. and then sieved into the grain size of from 297 μm to 1460 μm. 500 mg Of the granules were packed into a unit dosage form.

PREPARATION 3

Syrup 5 g Of 3-ethyl-2-(2-pyridylmethylthio)-4(3H)-quinazolinone, 30 g of refined sugar, 25 g of 70 w/v % D-sorbitol, 0.03 g of ethyl p-hydroxybenzoate and 0.015 g of propyl p-hydroxybenzoate were dissolved in 60 ml of warmed water. After the solution was cooled, a solution of 0.2 g of a flavor in 0.15 g of glycerol and 0.5 g of 96% ethanol was added. The whole mixture was diluted with water to balance 100 ml.

PREPARATION 4

Injectable solution 5 mg Of 3-ethyl-2-(2-pyridylmethylthio)-4(3H)-quinazolinone and 10 mg of sodium chloride were dissolved in sterilized distilled water to balance 1 ml.

PREPARATION 5

Suppository 20 g Of polyethylene glycol 4000 were added to a solution of 10 g of 3-ethyl-2-(2-pyridylmethylthio)-4(3H)-quinazolinone in 70 g of glycerol. The mixture was warmed and poured into a suppository mold and then cooled to give suppositories, each weighing 1.5 g.

What is claimed is:

1. A compound of formula (I)

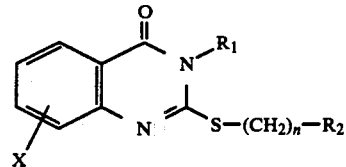

wherein R$_1$ is a hydrogen atom, a C$_1$-C$_6$ alkyl group or a phenyl group; R$_2$ is a (C$_1$-C$_4$) alkoxy substituted phenyl group, pyridyl, benzimidazolyl, furyl, thienyl or quinolyl; n is 1 or 2; or R$_2$ represents a geranyl group or a dipyridylmethyl group together with the group —(CH$_2$)n—; and X is a hydrogen atom, a C$_1$-C$_6$ alkyl group and pharmaceutically acceptable acid adition salts thereof, provided that when R$_1$ is phenyl, R$_2$ does not represent pyridyl, and further provided that when $R_1$ is $C_1$-$C_6$ alkyl, $R_2$ does not represent ($C_1$-$C_4$) alkoxy substituted phenyl.

2. A compound of claim 1 wherein $R_1$ is hydrogen, a $C_1$-$C_4$ alkyl group or phenyl.

3. A compound of claim 1 wherein $R_2$ is trimethoxyphenyl, pyridyl, benzimidazolyl, furyl, thienyl or quinolyl and n is 1 or 2.

4. A compound of claim 1 wherein $R_2$ represents a geranyl group or a dipyridylmethyl group together with the group — $(CH_2)n$— and n is 1 or 2.

5. A compound of claim 1 wherein X is hydrogen or a $C_1$-$C_4$ alkyl group.

6. A pharmaceutical composition which comprises as an active ingredient an effective amount of the compound of claim 1 or pharmaceutically acceptable acid addition salts thereof, optionally in admixture with additives for pharmaceutical preparation.

7. A pharmaceutical composition which comprises as an active ingredient an effective amount of the compound of claim 2 or pharmaceutically acceptable acid addition salts thereof, optionally in admixture with additives for pharmaceutical preparation.

8. A pharmaceutical composition which comprises as an active ingredient an effective amount of the compound of claim 3 or pharmaceutically acceptable acid addition salts thereof, optionally in admixture with additives for pharmaceutical preparation.

9. A pharmaceutical composition which comprises as an active ingredient an effective amount of the compound of claim 4 or pharmaceutically acceptable acid addition salts thereof, optionally in admixture with additives for pharmaceutical preparation.

10. A pharmaceutical composition which comprises as an active ingredient an effective amount of the compound of claim 5 or pharmaceutically acceptable acid addition salts thereof, optionally in admixture with additives for pharmaceutical preparation.

* * * * *

UNITED STATES PATENT AND TRADEMARK OFFICE
CERTIFICATE OF CORRECTION

PATENT NO. : 5,008,266
DATED : April 16, 1991
INVENTOR(S) : Takahashi et al.

It is certified that error appears in the above-identified patent and that said Letters Patent is hereby corrected as shown below:

Title page:

In the Title, delete "4(3H)-UINAZOLINONE", insert
-- 4(3H)-QUINAZOLINONE --

Claim 1 (column 14, second line from the bottom), delete "adition", insert -- addition --.

Signed and Sealed this

Tenth Day of November, 1992

Attest:

DOUGLAS B. COMER

Attesting Officer

Acting Commissioner of Patents and Trademarks